United States Patent
Kanai et al.

(10) Patent No.: US 11,840,512 B2
(45) Date of Patent: *Dec. 12, 2023

(54) OXAZOLE COMPOUND CRYSTAL

(71) Applicant: OTSUKA PHARMACEUTICAL CO., LTD., Tokyo (JP)

(72) Inventors: Naohiko Kanai, Osaka (JP); Takayuki Yasutomi, Osaka (JP); Ryosuke Hirota, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/859,675

(22) Filed: Jul. 7, 2022

(65) Prior Publication Data

US 2022/0411386 A1  Dec. 29, 2022

Related U.S. Application Data

(63) Continuation of application No. 17/044,892, filed as application No. PCT/JP2019/014730 on Apr. 3, 2019, now Pat. No. 11,414,391.

(30) Foreign Application Priority Data

Apr. 4, 2018 (JP) ............................ 2018-072717

(51) Int. Cl.
C07D 263/32 (2006.01)

(52) U.S. Cl.
CPC ........ C07D 263/32 (2013.01); *C07B 2200/13* (2013.01)

(58) Field of Classification Search
CPC ...... C07B 2200/13; A61K 31/421; A61K 9/06
See application file for complete search history.

(56) References Cited

FOREIGN PATENT DOCUMENTS

| JP | WO2017115780 | * | 7/2017 | ........... C07D 263/32 |
|---|---|---|---|---|
| WO | 2007/058338 A2 | | 5/2007 | |
| WO | WO-2007058338 A2 | * | 5/2007 | ........... A61K 31/421 |
| WO | 2014/034958 A1 | | 3/2014 | |
| WO | 2017/115780 A1 | | 7/2017 | |
| WO | WO-2017115780 A1 | * | 7/2017 | ........... A61K 31/421 |

OTHER PUBLICATIONS

International Search Report for PCT/JP2019/014730 dated Jun. 17, 2019. [PCT/ISA/210].
Joel Bernstein, "Chapter 4.5: Infrared Spectroscopy", Polymorphism in Molecular Crystals, 2002, International Union of Crystallography; 1st edition, pp. 125-131 (7 pages total).
Office Action dated Jun. 8, 2020 for the corresponding PK patent application No. 202/2019.
Office Action dated Aug. 3, 2021 in Japanese Application No. 2020-539109.
Office Action dated Jun. 27, 2022 by European Patent Office in European Application No. 19718465.8.
Regarding the revision of the Stability Test Guidelines for Stability, PMSB/ELD Notification No. 0603001, Chief Administrative Agency, Ministry of Health, Labour and Welfare, Jun. 3, 2003 (24 pages total).
English translation of "Regarding the revision of the Stability Test Guidelines", PMSB/ELD Notification No. 0603001, Chief Administrative Agency, Ministry of Health, Labour and Welfare, Jun. 3, 2003 (25 pages total).
Written Opinion for PCT/JP2019/014730 dated Jun. 17, 2019. [PCT/ISA/237].
Israeli Office Action dated Mar. 22, 2023 issued by Israeli Patent Office in Israeli Application No. 277730.
"FDA Guidance for Industry Q1A(R2) Stability Testing of New Drug Substances and Products", ICH, 2003, Revision 2, pp. 1-22 (25 pages total).
Zhang et al., "Polymorph Transformation of Solid Drugs", Acta Pharm Sin, 2015, vol. 50, No. 5, pp. 521-527 (8 pages total).
Office Action dated Jan. 24, 2023 from the Japanese Patent Office in Application No. 2021-196978.
Yamano, Mitsuhisa, "Approach to Crystal Polymorph in Process Research of New Drug", Society of Synthetic Organic Chemistry, Japan, 2007, vol. 65, No. 9, pp. 907-913 (21 total pages).
Terada, Katsuhide, "Application of Thermal Analysis to the Pharmaceutical Development", Netsu Sokutei, 2011, vol. 38, No. 2, pp. 46-53 (8 total pages).

\* cited by examiner

*Primary Examiner* — Brandon J Fetterolf
*Assistant Examiner* — Frank S. Hou
(74) *Attorney, Agent, or Firm* — Sughrue Mion, PLLC

(57) ABSTRACT

Provided is a crystal of a specific oxazole compound that has specific inhibitory activity against PDE4, and that shows excellent stability. Specifically, provided is a crystal of an oxazole compound represented by formula (5)

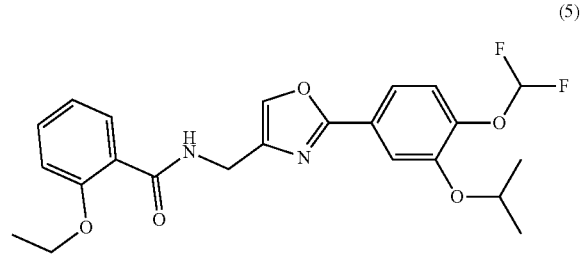

(5)

wherein the crystal has peaks at diffraction angles $2\theta(°)$ of $9.6\pm0.2$, $19.1\pm0.2$, and $21.2\pm0.2$ in an X-ray powder diffraction pattern measured using CuKα characteristic X-rays.

14 Claims, 4 Drawing Sheets

[Fig. 1]
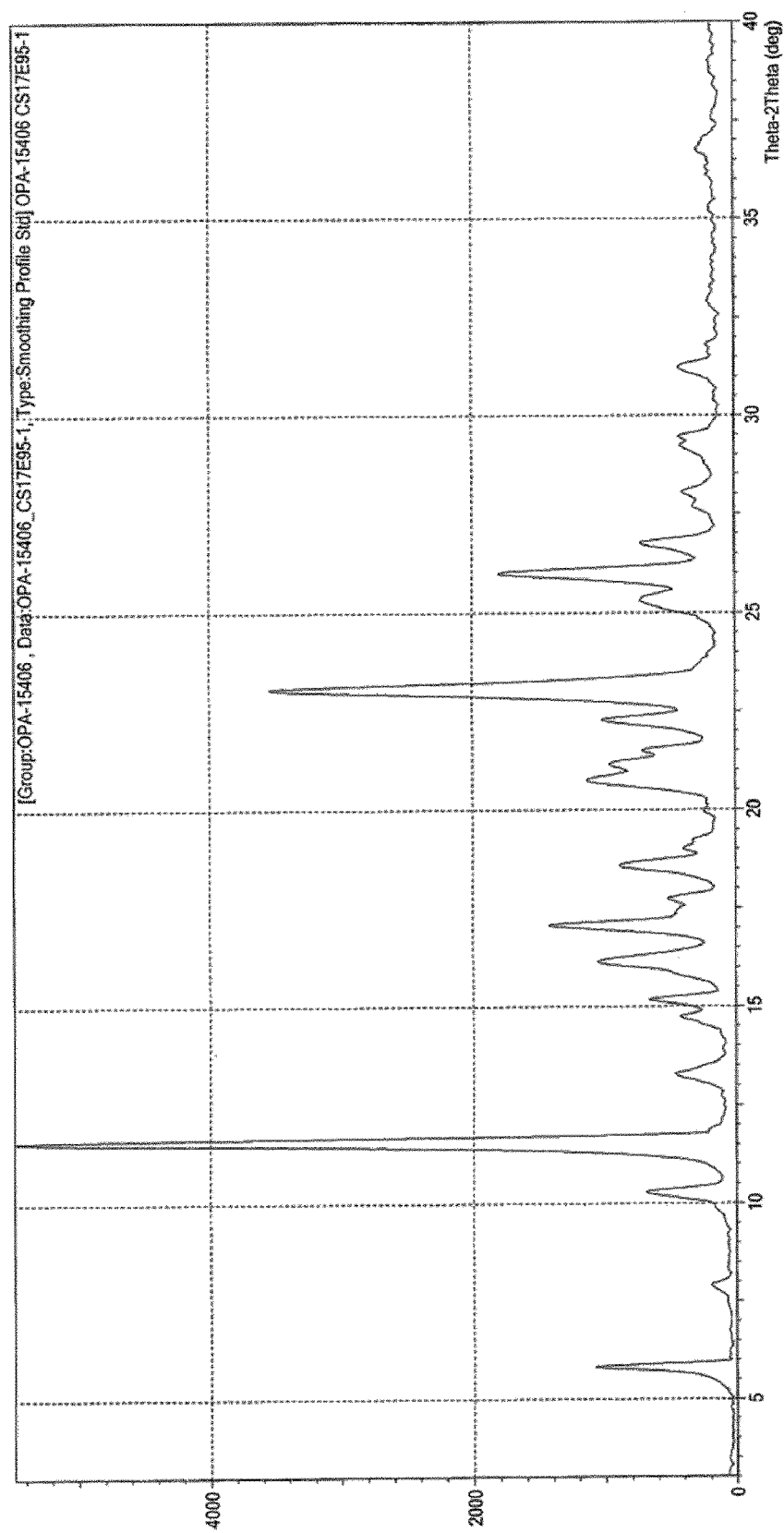

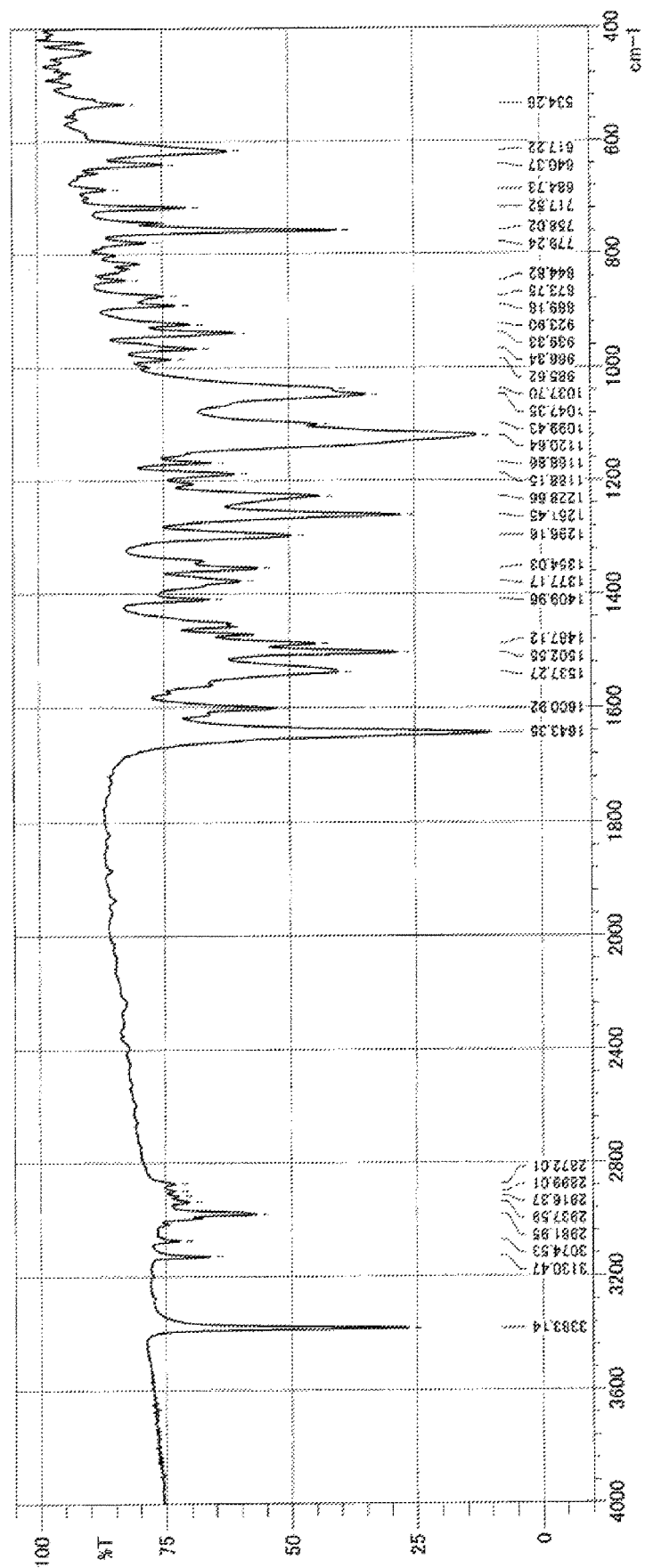
[Fig. 2]

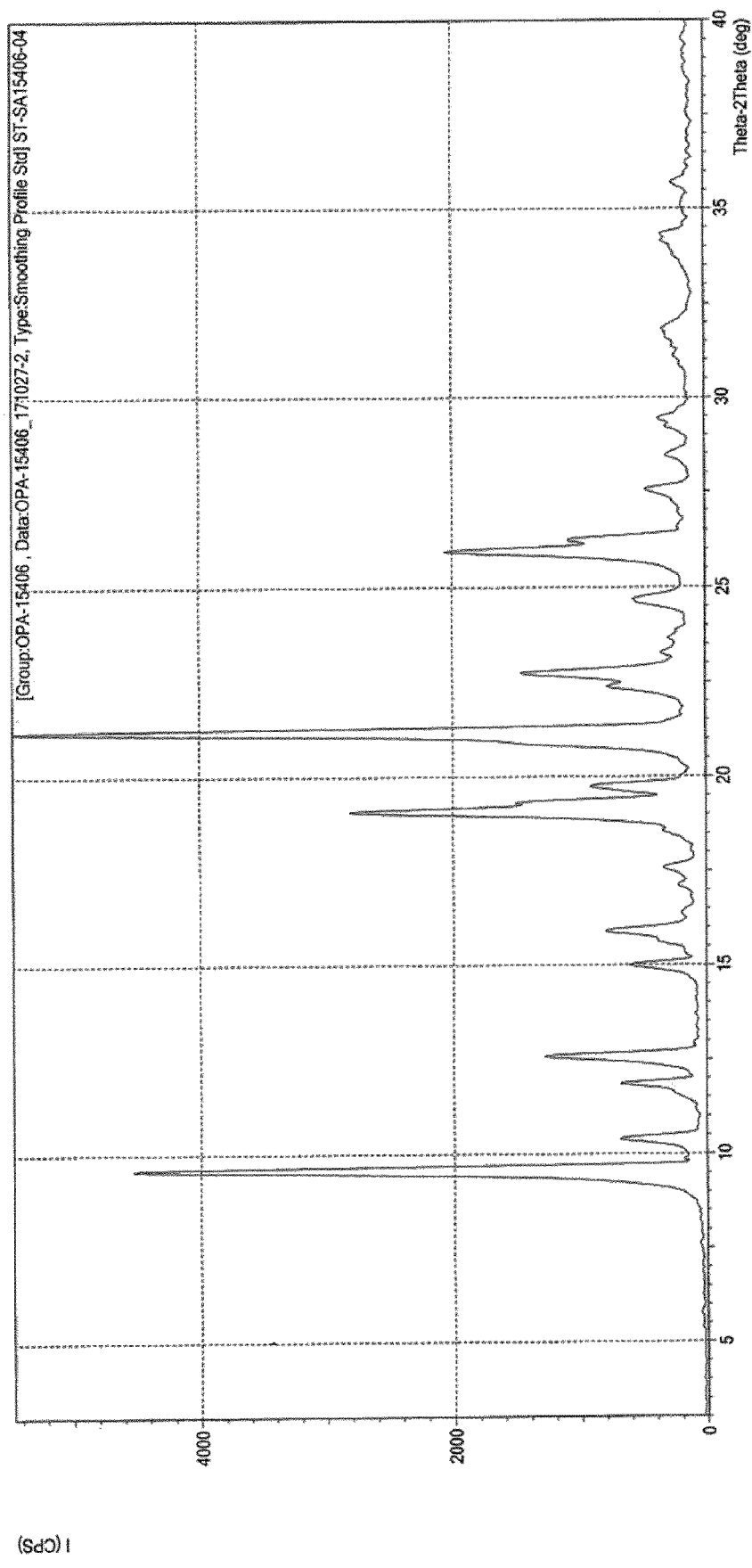
[Fig. 3]

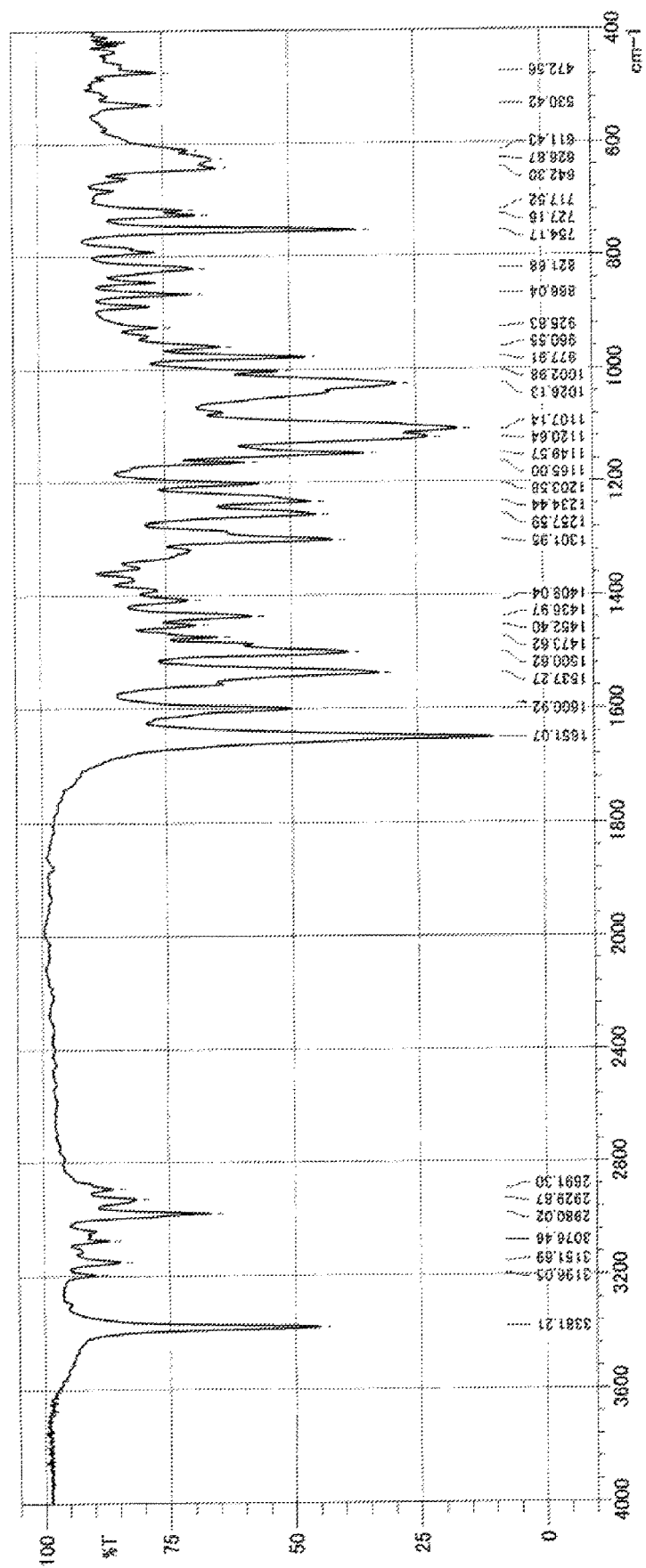
[Fig. 4]

OXAZOLE COMPOUND CRYSTAL

CROSS REFERENCE TO RELATED APPLICATIONS

This application is a Continuation Application of U.S. application Ser. No. 17/044,892 filed Oct. 2, 2020, which is a National Stage of International Application No. PCT/JP2019/014730 filed Apr. 3, 2019, claiming priority based on Japanese Patent Application No. 2018-072717 filed Apr. 4, 2018. The entire disclosures of the prior applications are incorporated herein by reference.

TECHNICAL FIELD

The present invention relates to a novel crystal of an oxazole compound, a method for producing the same, etc.

BACKGROUND ART

PTL 1 and 2 report an oxazole compound having specific inhibitory activity against phosphodiesterase 4 (PDE4), and a method for producing the oxazole compound. PDE4 is predominant in inflammatory cells. Inhibition of PDE4 increases intracellular cAMP levels, and increased cAMP levels down-regulate inflammatory response through expression regulation of TNF-α, IL-23, or other inflammatory cytokines. Increases in cAMP levels also increase anti-inflammatory cytokines, such as IL-10. Thus, the oxazole compound is thought to be suitable for use as an anti-inflammatory agent. For example, the oxazole compound is thought to be useful for reducing or eliminating eczema or dermatitis, including atopic dermatitis. PTL 3 discloses an ointment that stably contains an oxazole compound having specific inhibitory activity against PDE4, and that can be efficiently absorbed into the skin. The disclosures of PTL 1 to 3 are hereby incorporated by reference in their entirety.

CITATION LIST

Patent Literature

PTL 1: WO2007/058338 (JP2009-515872A)
PTL 2: WO2014/034958 (JP2015-528433A)
PTL 3: WO2017/115780

SUMMARY OF INVENTION

Technical Problem

An object of the present invention is to provide a crystal of an oxazole compound (specifically, an oxazole compound represented by formula (5) below) that has specific inhibitory activity against PDE4, and that shows more excellent stability.

Solution to Problem

The present inventors found a method for preparing a novel type of previously unreported crystal, using a specific oxazole compound having inhibitory activity against PDE4, and further found that the novel type of crystal has excellent stability. The inventors made further modifications, and completed the present invention.

Specifically, the present invention encompasses, for example, the following subject matter.

Item 1. A crystal of an oxazole compound represented by formula (5)

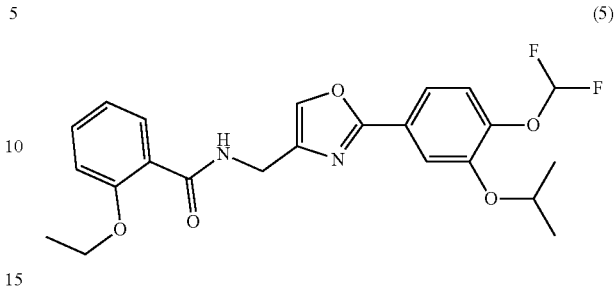

wherein the crystal has peaks at diffraction angles $2\theta(°)$ of 9.6±0.2, 19.1±0.2, and 21.2±0.2 in an X-ray powder diffraction pattern measured using CuKα characteristic X-rays.

Item 2. The crystal according to Item 1, wherein the crystal further has one, two, or three peaks at one, two, or three diffraction angles $2\theta(°)$ selected from the group consisting of 12.6±0.2, 22.8±0.2, and 26.0±0.2 in the X-ray powder diffraction pattern measured using CuKα characteristic X-rays.

Item 3. The crystal according to Item 2, wherein the crystal further has one or more peaks at one or more diffraction angles $2\theta(°)$ selected from the group consisting of 10.4±0.2, 11.9±0.2, 15.0±0.2, 15.9±0.2, 19.7±0.2, 24.7±0.2, and 27.6±0.2 in the X-ray powder diffraction pattern measured using CuKα characteristic X-rays.

Item 4. A crystal of an oxazole compound represented by formula (5)

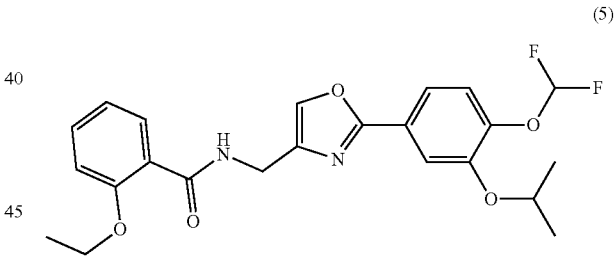

wherein the crystal has infrared absorption bands at wavenumbers $(cm^{-1})$ of 3380±5, 2980±5, 1651±2, 1501±2, 1258±2, 1121±2, and 754±2 in an infrared absorption spectrum measured by a potassium bromide disk method.

Item 5. The crystal according to any one of Items 1 to 3, wherein the crystal has infrared absorption bands at wavenumbers $(cm^{-1})$ of 3380±5, 2980±5, 1651±2, 1501±2, 1258±2, 1121±2, and 754±2 in an infrared absorption spectrum measured by a potassium bromide disk method.

Item 6. The crystal according to Item 4 or 5, wherein the crystal further has one or more infrared absorption bands at one or more wavenumbers $(cm^{-1})$ selected from the group consisting of 1601±2, 1537±2, 1302±2, 1234±2, 1107±2, 1026±2, and 627±2 in the infrared absorption spectrum measured by the potassium bromide disk method.

Item 7. The crystal according to any one of Items 1 to 6, wherein the crystal has a melting point of 75 to 90° C.

Item 8. A crystal of an oxazole compound represented by formula (5)

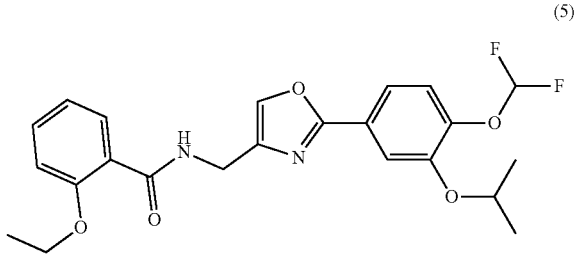 [SMILES: CCOc1ccccc1C(=O)NCc1coc(-c2ccc(OC(F)F)c(OC(C)C)c2)n1]

(5)

wherein the crystal has a melting point of 75 to 90° C.

Item 9. A pharmaceutical composition comprising the crystal according to any one of Items 1 to 8.

Item 10. The pharmaceutical composition according to Item 9, for use in the treatment and/or prevention of eczema or dermatitis (preferably atopic dermatitis).

Item 11 The pharmaceutical composition according to Item 9 or 10, which is an ointment.

Advantageous Effects of Invention

A more stable crystal of a specific oxazole compound having inhibitory activity against PDE4 can be provided. In particular, since the crystal has a higher melting point than a crystal of the conventional specific oxazole compound, it has high thermal stability, and is advantageous.

BRIEF DESCRIPTION OF DRAWINGS

FIG. 1 shows an X-ray powder diffraction pattern of a type A crystal of compound (5), which is measured using CuKα characteristic X-rays.

FIG. 2 shows an infrared absorption spectrum of a type A crystal of compound (5), which is measured by a potassium bromide disk method.

FIG. 3 shows an X-ray powder diffraction pattern of a type B crystal of compound (5), which is measured using CuKα characteristic X-rays.

FIG. 4 shows an infrared absorption spectrum of a type B crystal of compound (5), which is measured by a potassium bromide disk method.

DESCRIPTION OF EMBODIMENTS

Embodiments of the present invention are detailed below.
The crystal of the oxazole compound in the present invention includes a crystal of the oxazole compound represented by formula (5) below.

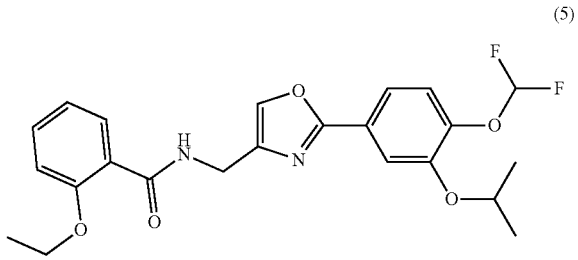 [SMILES: CCOc1ccccc1C(=O)NCc1coc(-c2ccc(OC(F)F)c(OC(C)C)c2)n1]

(5)

The oxazole compound has specific inhibitory activity against PDE4, and is effective as an anti-inflammatory agent etc. In this specification, the oxazole compound represented by formula (5) is sometimes referred to as compound (5). Compound (5) is N-[2-(4-difluoro methoxy-3-isopropoxy phenyl)oxazol-4-ylmethyl]-2 ethoxybenzamide.

Compound (5) can be produced by a known method (for example, a method described in any one of PTL 1 to 3). However, crystal forms of compound (5) produced by known methods are different from the crystal form of compound (5) encompassed in the present invention. In this specification, the former crystal form is sometimes referred to as type A, and the latter crystal form is sometimes referred to as type B. Specifically, the crystal of compound (5) produced by a known method is a type A crystal, and the crystal of compound (5) encompassed in the present invention is a type B crystal.

The type B crystal is a crystal of compound (5) having one or more of the following features. Among features (i) to (iii) below, the type B crystal preferably has at least one feature, more preferably has at least two features (i.e., features (i) and (ii), features (ii) and (iii), or features (iii) and (i)), and still more preferably has all three features.

Feature (i): Characteristic X-Ray Powder Diffraction Pattern

The type B crystal preferably has peaks at diffraction angles $2\theta(°)$ of 9.6±0.2, 19.1±0.2, and 21.2±0.2 in the X-ray powder diffraction pattern measured by CuKα characteristic X-rays. Of these three peaks, the intensity of the peak at a diffraction angle $2\theta(°)$ of 19.1±0.2 (sometimes referred to as peak [12]) is preferably the lowest. The intensity of the peak at a diffraction angle $2\theta(°)$ of 21.2±0.2 (sometimes referred to as peak [16]) is preferably the largest. The peak at a diffraction angle $2\theta(°)$ of 9.6±0.2 is sometimes referred to as peak [2].

The rate of the intensity of peak [12] and peak [16](peak [16]/peak [12]) is preferably about 1.5 to 2.5, more preferably about 1.6 to 2.4 or 1.7 to 2.3, and still more preferably about 1.8 to 2.2 or about 1.9 to 2.1. The rate of the intensity of peak [12] and peak [2] (peak [2]/peak [12]) is preferably about 1.5 to 1.75.

It is further preferable to have one, two, or three peaks at one, two, or three diffraction angles $2\theta(°)$ selected from the group consisting of 12.6±0.2, 22.8±0.2, and 26.0±0.2, in addition to the above three peaks (peaks [2], [12], and [16]). The peak at a diffraction angle $2\theta(°)$ of 12.6±0.2 is sometimes referred to as peak [6]. The peak at a diffraction angle $2\theta(°)$ of 22.8±0.2 is sometimes referred to as peak [18]. The peak at a diffraction angle $2\theta(°)$ of 26.0±0.2 is sometimes referred to as peak [20].

In the most preferable embodiment, the type B crystal has all of peaks [6], [18], and [20], in addition to peaks [2], [12], and [16]. In this case, the intensity of each of peaks [6], [18], and [20] is preferably lower than the intensity of peak [12]. In addition, the intensity of peak [20] is preferably the largest among the intensity of peaks [6], [18], and [20].

In addition to the above four to six peaks (three peaks of peaks [2], [12], and [16]; and one, two, or three peaks selected from the group consisting of peaks [6], [18], and [20]), it is further preferable to have one or more peaks at one or more (2, 3, 4, 5, 6, or 7) diffraction angles $2\theta(°)$ selected from the group consisting of 10.4±0.2, 11.9±0.2, 15.0±0.2, 15.9±0.2, 19.7±0.2, 24.7±0.2, and 27.6±0.2. The intensity of each of these one to seven peaks is preferably lower than the intensity of each the four to six peaks mentioned above. Particularly preferred is a type B crystal having peaks [2], [12], [16], and peaks [6], [18], and [20];

as well as peaks at diffraction angles 2θ(°) of 10.4±0.2, 11.9±0.2, 15.0±0.2, 15.9±0.2, 19.7±0.2, 24.7±0.2, and 27.6±0.2.

Feature (ii): Characteristic Infrared Absorption Spectrum

The type B crystal preferably has infrared absorption bands at wavenumbers ($cm^{-1}$) of 3380±5, 2980±5, 1651±2, 1501±2, 1258±2, 1121±2, and 754±2 in the infrared absorption spectrum measured by a potassium bromide disk method. Of these infrared absorption bands, an infrared absorption band at a wavenumber ($cm^{-1}$) of 1651±2 is particularly a band characteristic to the type B crystal. These infrared absorption bands are derived from infrared absorption of characteristic functional groups present in compound (5), which is more specifically explained below. (The wavelength described to the right of the slash "/" in the following description is the wavelength of the infrared absorption band of the type A crystal described below.)

3380 ($cm^{-1}$): Secondary amide N—H Stretching vibration
2980 ($cm^{-1}$): —$CH_2$ Stretching vibration
1651/1643 ($cm^{-1}$): Amide C═O Stretching vibration
1501/1503 ($cm^{-1}$): Aromatic C═C Stretching vibration
1258/1261, 1121/1119 ($cm^{-1}$): —$CF_2$ Stretching vibration
754/758 ($cm^{-1}$): Benzene C—H Out-of-plane bending vibration In addition to such characteristic infrared absorption bands, the type B crystal preferably has one or more infrared absorption bands at one or more (2, 3, 4, 5, 6, or 7) wavenumbers ($cm^{-1}$) selected from the group consisting of 1601±2, 1537±2, 1302±2, 1234±2, 1107±2, 1026±2, and 627±2.

In the infrared absorption spectrum, the error of the wavenumber ($cm^{-1}$) of one or more (2, 3, 4, 5, 6, 7, 8, 9, 10, 11, 12, or 13) infrared absorption bands may be ±4, ±3, ±2, or ±1.

Feature (iii): Characteristic Melting Point

The melting point of the type B crystal is preferably 75 to 90° C. The lower limit of this range may be 76° C., 77° C., 78° C., 79° C., or 80° C. The upper limit of this range may be 89° C., 88° C., 87° C., 86° C., 85° C., or 84° C. The melting point is preferably 77 to 88° C., more preferably 78 to 86° C., still more preferably 79 to 85° C., and particularly preferably 80 to 84° C.

The melting point is the value measured according to Method 1 in Section 2.60 of the Japanese Pharmacopoeia, Seventeenth Edition.

The type B crystal can be prepared by allowing the type A crystal to stand for a long period of time at a temperature higher than room temperature. More specifically, the type B crystal can be prepared by allowing the type A crystal to stand at preferably 40 to 60° C., more preferably 45 to 55° C., and still more preferably at 48 to 52° C., for preferably 3 months or more, and more preferably 4 months or more or 5 months or more. The upper limit of the static period is not particularly limited, as long as the type B crystal can be obtained; and it is, for example, about 6 or 7 months. The type A crystal is preferably allowed to stand in sealed or tightly sealed containers. Moreover, the type A crystal is preferably allowed to stand under a condition that is unaffected by light (e.g., a light-shielding condition; more specifically, in a light-blocking amber bottle).

The type A crystal can be prepared by a known method as described above, for example, by a method described in any of PTL 1 to 3. Although there is no particular limitation, the type A crystal can be prepared by preparing compound (5) according to the reaction formula described in PTL 3, and precipitating the crystal of compound (5). The resulting precipitated crystal can be dried, and then used as the type A crystal. The dried type A crystal is particularly preferred as a type A crystal that is allowed to stand at a temperature higher than room temperature for a long period of time, and used for preparing the type B crystal.

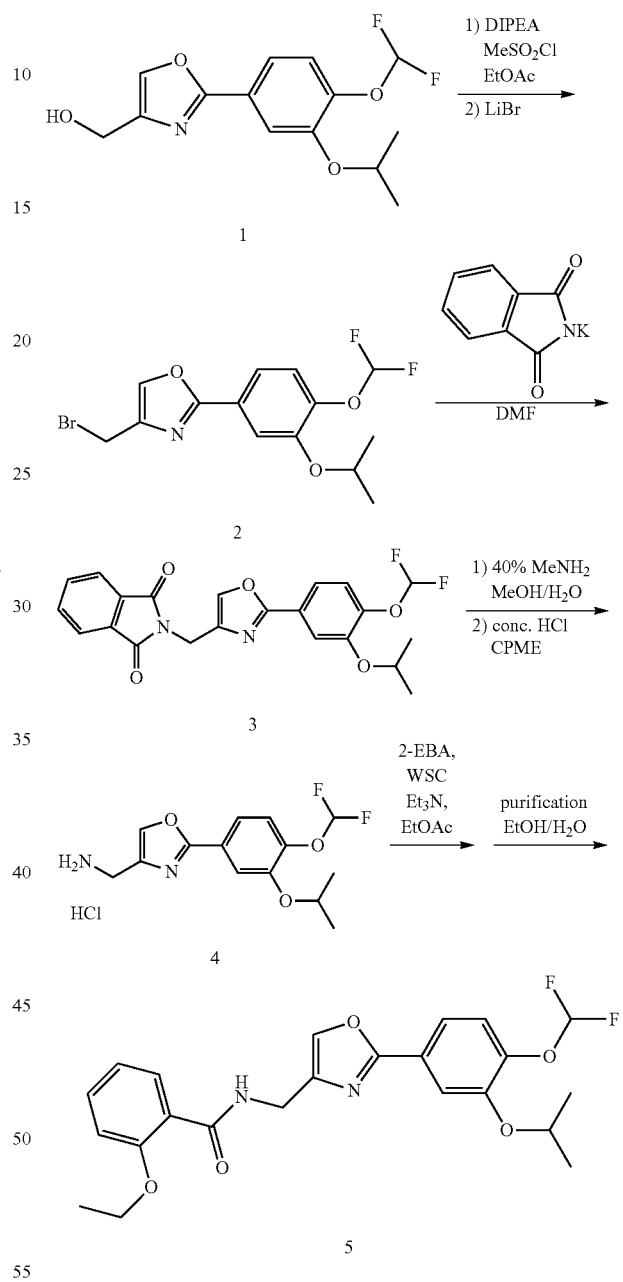

DIPEA: Diisopropylethylamine, CPME: Cyclopentyl methyl ether, DMF: N,N-dimethylformamide, 2-EBA: 2-Ethoxybenzoic acid, WSC: 1-Ethyl-3-(3-dimethylaminopropyl) carbodiimide hydrochloride The X-ray powder diffraction pattern, infrared absorption spectrum, and melting point of the type A crystal are described below. The type A crystal particularly has characteristic peaks at diffraction angles 2θ(°) of 5.8±0.2, 11.6±0.2, 17.1±0.2, 23.1±0.2, and 26.1±0.2 in the X-ray powder diffraction pattern measured using CuKα characteristic X-rays. The type A crystal may further have one or more peaks at one or more diffraction angles 2θ(°) selected from the group consisting of 10.2±0.2, 13.2±0.2, 16.1±0.2, 18.5±0.2, 22.2±0.2, and 26.7±0.2. The type A crystal particularly has infrared absorption bands at wavenumbers ($cm^{-1}$) of 3380±5, 2980±5, 1643±2, 1503±2, 1261±2, 1119±2, and 758±2 in the infrared absorption spectrum measured by a potassium bromide disk method. The type A crystal may further have one or more infrared absorption bands at one or more wavenumbers ($cm^{-1}$) selected from the group consisting of 1601±2, 1537±2, 1296±2, 1229±2, 1047±2, 939±2, and 617±2. The melting point of the type A crystal (measured in accordance with Method 1 in Section 2.60 of the Japanese Pharmacopoeia, Seventeenth Edition) is about 56 to 60° C.

The present invention also comprises a pharmaceutical composition containing the type B crystal. The pharmaceutical composition, for example, contains a pharmaceutically acceptable carrier and the type B crystal. Such carriers are not particularly limited, and known carriers can be used. The pharmaceutical composition is sometimes referred to as the pharmaceutical composition of the present invention.

The pharmaceutical composition of the present invention is particularly effective for reducing or eliminating eczema and dermatitis, in particular for reducing or eliminating atopic dermatitis. The pharmaceutical composition of the present invention can be used as a preventing agent and/or treating agent of these diseases.

The form of the pharmaceutical composition of the present invention is not particularly limited. Examples include externally applied agents for the skin, oral formulations, injections, and the like. Of these, externally applied agents for the skin are preferred, and ointments are particularly preferred. In an ointment, it is preferable that type B crystal (I) is dissolved in a base component, and that the base component comprises ointment base (III) and solvent (II) for dissolving compound (5).

More preferred is an ointment wherein solvent (II) containing dissolved type B crystal (I) is dissolved or dispersed in the form of droplets in ointment base (III).

Type B crystal (I) may be dissolved in solvent (II) by heating. Type B crystal (I) is preferably dissolved by heating at a temperature higher than the melting point of type B crystal. For example, heating and dissolving can be performed at 75° C. or higher, 76° C. or higher, 77° C. or higher, 78° C. or higher, 79° C. or higher, 80° C. or higher, 81° C. or higher, 82° C. or higher, 83° C. or higher, 84° C. or higher, 85° C. or higher, 86° C. or higher, 87° C. or higher, 88° C. or higher, 89° C. or higher, or 90° C. or higher. The upper limit of the heating temperature is not particularly limited, as long as the effects of compound (5) are attained. For example, the temperature is 100° C. or lower, 99° C. or lower, 98° C. or lower, 97° C. or lower, 96° C. or lower, 95° C. or lower, 94° C. or lower, 93° C. or lower, 92° C. or lower, or 91° C. or lower.

Although there is no particular limitation, type B crystal (I) is present in the ointment in an amount of preferably 0.01 to 10 parts by weight, more preferably 0.05 to 7.5 parts by weight, still more preferably 0.1 to 5 parts by weight, per 100 parts by weight of the ointment.

As stated above, type B crystal (I) is preferably dissolved in solvent (II). The solvent is preferably a polar compound that is a liquid at room temperature. Specific examples of the solvent include ethylene carbonate, propylene carbonate, benzyl alcohol, triacetin, diethyl sebacate, diisopropyl sebacate, diethyl adipate, diisopropyl adipate, isostearic acid, olive oil, hexyldodecanol, decyl oleate, isostearyl alcohol, and isopropyl myristate. Ethylene carbonate, propylene carbonate, benzyl alcohol, and triacetin are more preferable, and propylene carbonate and triacetin are still more preferable. Of these, propylene carbonate is preferable. These solvents can be used singly, or in a combination of two or more. In particular, it is preferable to use ethylene carbonate or propylene carbonate alone, or a combination of ethylene carbonate or propylene carbonate with benzyl alcohol and/or triacetin.

Solvent (II) is present in the ointment in an amount of preferably more than 2 parts by weight, more preferably 2.1 parts by weight or more, and still more preferably 2.2 parts by weight or more, per part by weight of type B crystal (I). The upper limit of the amount of solvent (II) is not particularly limited, as long as the effect of the present invention is produced. For example, the upper limit is preferably 30 parts by weight or less, more preferably 20 parts by weight or less, and still more preferably 15 parts by weight or less.

Solvent (II) is present in the ointment in an amount of preferably 0.1 to 50 parts by weight, more preferably 0.2 to 25 parts by weight, and still more preferably 0.5 to 20 parts by weight, per 100 parts by weight of the ointment.

A solution of the type B crystal in the solvent is preferably dissolved or dispersed in the form of droplets in ointment base (III), and more preferably dispersed in the form of droplets in ointment base (III).

Known ointment bases for use in the production of ointments can be used as ointment base (III). Examples of ointment bases include hydrocarbons, and more specific examples include grease bases, particularly natural wax, petroleum wax, and other hydrocarbons. Examples of natural wax include beeswax (e.g., unbleached beeswax, non-chemically bleached beeswax, and chemically bleached beeswax), and carnauba wax. Examples of petroleum wax include paraffin and microcrystalline wax. Examples of other hydrocarbons include liquid paraffin and petrolatum (e.g., white petrolatum and yellow petrolatum). These ointment bases can be used singly, or in a combination of two or more.

Ointment base (III) is present in the ointment in an amount of preferably 5 to 5000 parts by weight, more preferably 10 to 2500 parts by weight, and still more preferably 20 to 1000 parts by weight, per part by weight of type B crystal (I).

Ointment base (III) is present in the ointment in an amount of preferably 50 to 99 parts by weight, more preferably 70 to 98 parts by weight, and still more preferably 80 to 97 parts by weight, per 100 parts by weight of the ointment.

Ointment base (III) preferably comprises at least beeswax. The beeswax for use is preferably beeswax that is not chemically bleached; including, for example, beeswax that is non-chemically bleached (non-chemically bleached beeswax), and beeswax that is not bleached (unbleached beeswax).

The beeswax is present in the ointment in an amount of preferably 0.05 to 50 parts by weight, more preferably 0.1 to 40 parts by weight, and still more preferably 0.2 to 35 parts by weight, per part by weight of type B crystal (I).

The beeswax is present in the ointment in an amount of preferably 0.1 to 10 parts by weight, more preferably 0.2 to 9 parts by weight, still more preferably 0.4 to 8 parts by weight, even still more preferably 0.5 to 7.5 parts by weight, and particularly preferably 1 to 5 parts by weight, per 100 parts by weight of the ointment.

When other ointment bases are combined with beeswax, the combination is not particularly limited. However, for example, the combination preferably comprises beeswax and at least one member selected from the group consisting of petrolatum (preferably white petrolatum), liquid paraffin, and paraffin.

In addition to the ointment base, the ointment may comprise other additives for use in ointments (in particular, pharmaceutical additives), such as aroma components, colorants, preservatives, absorption promoters including higher alkene acids (e.g., oleic acid), or medicaments effective for treating other skin diseases.

As stated above, the ointment of the present invention is preferably an ointment wherein solvent (II), in which type B crystal (I) is dissolved, is dissolved or dispersed in the form of droplets in ointment base (III). Examples of the method for producing this ointment include a method comprising preparing a solution of component (I) in component (II), and mixing the solution with component (III) with stirring. Mixing with stirring can be performed with, for example, a homomixer, a paddle mixer, or a combination of these mixers.

In the use of multiple types of ointment bases (component (III)), it is preferable to mix the multiple ointment bases beforehand. In the formulation of component (III) containing multiple types of ointment bases, it is preferable to mix the ointment bases with heating to melt the solids, such as beeswax. For example, when beeswax and other ointment bases are used in combination, the beeswax and other ointment bases are preferably mixed beforehand, preferably with heating.

In the case of an ointment wherein component (II), in which component (I) is dissolved, is dispersed in the form of droplets in component (III), the particle size of the droplets observed with a polarizing microscope is 100 µm or less, preferably about 40 µm or less, more preferably about 25 µm or less, and still more preferably about 20 µm or less. In particular, there exist preferably no droplets having a particle size of more than 100 µm, more preferably no droplets having a particle size of more than 40 µm, still more preferably no droplets having a particle size of more than 25 µm, and even still more preferably no droplets having a particle size of more than 20 µm. A desired mean particle size of the droplets is achieved by adjusting the stirring rate at which the solution is mixed with component (III) with stirring.

In this specification, the term "comprising" includes "consisting essentially of" and "consisting of." The present invention covers all combinations of the elements described in this specification.

The characteristics (properties, structures, functions, etc.) that are explained in the embodiments of the present invention can be combined in any manner to specify the subject matter included in the present invention. Specifically, the present invention covers all of the subject matter that includes various combinations of the combinable characteristics described in this specification.

Examples

The present invention is described below in more detail. However, the present invention is not limited to the following Examples. In the following reaction schemes, when a compound is denoted numerically, the compound may be referred to as "compound (numerical number)." For example, a compound denoted as "3" may be referred to as "compound (3)." Further, in the following reaction schemes, the compound denoted as "5" is the same as compound (5) described above.

Synthesis of Oxazole Compound (Type A Crystal)

Compound (5) (white powder) was prepared in accordance with the method disclosed in Example 352 of PTL 1 (WO2007/058338).

Data of Compound (5)

N-({2-[4-(difluoromethoxy)-3-isopropoxyphenyl]oxazol-4-yl}methyl)-2-ethoxybenzamide: white powder.

$^1$H NMR (400 MHz, CDCl3): δ=8.56 (br s, 1H, NH), 8.23 (dd, J=7.6 Hz, 1.6 Hz, 1H, ArH), 7.66 (s, 1H, ArH), 7.63 (d, J=2.0 Hz, 1H, ArH), 7.58 (dd, J=8.4 Hz, 2.0 Hz, 1H, ArH), 7.44-7.39 (m, 1H, ArH), 7.21 (d, J=8.0 Hz, 1H, ArH), 7.08-7.04 (m, 1H, ArH), 6.94 (d, J=8.0 Hz, 1H, ArH), 6.61 (t, J=75.2 Hz, 1H, CHF$_2$), 4.68 (sept, J=6.0 Hz, 1H, CH), 4.62 (d, J=6.0 Hz, 2H, CH$_2$), 4.17 (q, J=6.93, 2H, CH$_2$), 1.48 (t, J=7.2 Hz, 3H, CH$_3$), 1.39 (d, J=5.6 Hz, 6H, 2CH$_3$).

The X-ray powder diffraction pattern of the obtained white powder of compound (5) was measured using CuKα characteristic X-rays. More specifically, the measurement was conducted under the following conditions.

Measurement device—XRD-6000 (Shimadzu Corporation)

Operating conditions—Voltage: 35.0 kV, Current: 20.0 mA, Sampling Pitch: 0.0200°

FIG. 1 and Table 1 show the measurement results.

TABLE 1

| peak no. | 2Theta (deg) | d (A) | I/I1 | FWHM (deg) | Intensity (Counts) | Integrated Int (Counts) |
|---|---|---|---|---|---|---|
| # Strongest 3 peaks | | | | | | |
| 1 | 4 | 11.5469 | 7.65742 | 100 | 0.2406 | 869 | 11021 |
| 2 | 19 | 23.0346 | 3.85799 | 63 | 0.3511 | 544 | 11213* |
| 3 | 21 | 25.9597 | 3.42952 | 30 | 0.3355 | 262 | 4458 |
| # Peak Data List | | | | | | |
| 1 | 5.8157 | 15.18438 | 19 | 0.1860 | 169 | 1999 |
| 2 | 10.2509 | 8.62243 | 11 | 0.2728 | 93 | 1422 |
| 3 | 11.1800 | 7.90788 | 9 | 0.1714 | 77 | 1471 |
| 4 | 11.5469 | 7.65742 | 100 | 0.2406 | 869 | 11021 |
| 5 | 13.2725 | 6.66548 | 7 | 0.3450 | 59 | 1156 |
| 6 | 14.7100 | 6.01718 | 6 | 0.2600 | 49 | 759 |
| 7 | 15.1487 | 5.84390 | 10 | 0.2254 | 85 | 1002 |
| 8 | 15.8200 | 5.59740 | 6 | 0.2400 | 48 | 679 |
| 9 | 16.1346 | 5.48896 | 16 | 0.3827 | 139 | 2601 |
| 10 | 17.0431 | 5.19836 | 23 | 0.2738 | 199 | 3292 |
| 11 | 17.4200 | 5.08673 | 4 | 0.0000 | 39 | 0 |
| 12 | 17.7200 | 5.00128 | 6 | 0.2450 | 53 | 899 |
| 13 | 18.5686 | 4.77458 | 13 | 0.3293 | 116 | 2029 |
| 14 | 19.0800 | 4.64775 | 4 | 0.3600 | 35 | 612 |
| 15 | 20.7400 | 4.27935 | 17 | 0.4300 | 144 | 2826 |
| 16 | 21.1400 | 4.19927 | 13 | 0.4134 | 115 | 2014 |
| 17 | 21.4800 | 4.13356 | 9 | 0.2216 | 74 | 844 |
| 18 | 22.2421 | 3.99362 | 14 | 0.3008 | 124 | 2136 |
| 19 | 23.0346 | 3.85799 | 63 | 0.3511 | 544 | 11211 |
| 20 | 25.2853 | 3.51945 | 10 | 0.5627 | 85 | 2603 |
| 21 | 25.9597 | 3.42952 | 30 | 0.3355 | 262 | 4458 |
| 22 | 26.5000 | 3.36081 | 4 | 0.2240 | 35 | 412 |
| 23 | 26.7020 | 3.33585 | 10 | 0.3040 | 90 | 1212 |
| 24 | 27.6400 | 3.22473 | 3 | 0.2000 | 26 | 351 |
| 25 | 28.0070 | 3.18331 | 4 | 0.2740 | 39 | 598 |
| 26 | 29.2200 | 3.05386 | 5 | 0.4480 | 41 | 855 |
| 27 | 29.4600 | 3.02952 | 5 | 0.1658 | 46 | 405 |
| 28 | 31.1971 | 2.86468 | 5 | 0.3408 | 46 | 1047 |

The infrared absorption spectrum of the obtained white powder of compound (5) was measured by the potassium bromide disk method. More specifically, the measurement was conducted under the following conditions.

Measurement device—IR Prestige-21 (Shimadzu Corporation)

Operating conditions—Cumulative number: 16, Resolution: 4 cm$^{-1}$

FIG. 2 shows the measurement results.

The melting point of the obtained white powder of compound (5) was measured in accordance with Method 1 in Section 2.60 of the Japanese Pharmacopoeia, Seventeenth Edition. More specifically, the measurement was conducted under the following conditions.

Measurement device—M-565 (BUCHI)

Operating conditions—The white powder of compound (5) was placed in a dry capillary tube to form a layer with a thickness of 2.5 to 3.5 mm. The bath fluid was gradually heated to 48° C., and the capillary tube containing the white powder was inserted. Subsequently, the temperature was increased at a rate of about 3° C. per minute, and when the temperature reached 53° C., the temperature was increased at a rate of about 1° C. per minute; the samples were then observed.

The measurement results confirmed that the melting point of the white powder (type A crystal) of compound (5) was about 56 to 60° C.

The crystals of compound (5) prepared in accordance with the method disclosed in PTL 2 (WO2014/034958) (in particular, Example 1 (1-10): compound 1) and the method disclosed in PTL 3 (WO2017/115780) (in particular, Production Example 4 (compound (11)) using the thus-obtained type A crystal as a seed crystal both also had the same characteristics as above, and thus were considered to be type A crystals.

Type B Crystal Preparation 1

The type A crystal (12 g) was placed in an amber glass bottle. The glass bottle was sealed, and stored for 3 months in an incubator (50±2° C.). The X-ray powder diffraction pattern and the infrared absorption spectrum of the powder (crystal) collected after storage were measured as above. FIG. 3 and Table 2 show the X-ray powder diffraction pattern, and FIG. 4 shows the infrared absorption spectrum. The melting point was also measured as in the above method, except that "48° C." was changed to "72° C.," and "53° C." was changed to "77° C." The melting point was found to be about 80 to 84° C.

TABLE 2

| peak no. | 2Theta (deg) | d (A) | I/I1 | FWHM (deg) | Intensity (Counts) | Integrated Int (Counts) |
|---|---|---|---|---|---|---|
| # Strongest 3 peaks | | | | | | |
| 1 | 16 | 21.1479 | 4.19772 | 100 | 0.2253 | 876 | 9915 |
| 2 | 2 | 9.5562 | 9.24764 | 82 | 0.2303 | 717 | 8537 |
| 3 | 12 | 19.0600 | 4.65258 | 50 | 0.2757 | 437 | 5663 |
| # Peak Data List | | | | | | |
| 1 | 9.1600 | 9.64672 | 6 | 0.2200 | 54 | 1412 |
| 2 | 9.5562 | 9.24764 | 82 | 0.2303 | 717 | 8537 |
| 3 | 10.3752 | 8.51941 | 11 | 0.2162 | 99 | 1244 |
| 4 | 11.5800 | 7.63560 | 3 | 0.2934 | 28 | 456 |
| 5 | 11.8351 | 7.47159 | 11 | 0.1837 | 97 | 881 |
| 6 | 12.5573 | 7.04346 | 22 | 0.2259 | 194 | 2554 |
| 7 | 14.9711 | 5.91282 | 9 | 0.2178 | 83 | 1024 |
| 8 | 15.6200 | 5.66862 | 5 | 0.2134 | 42 | 500 |
| 9 | 15.8818 | 5.57576 | 12 | 0.2487 | 109 | 1469 |
| 10 | 17.5600 | 5.04649 | 4 | 0.2500 | 37 | 688 |
| 11 | 18.5400 | 4.78189 | 4 | 0.2600 | 34 | 765 |
| 12 | 19.0600 | 4.65258 | 50 | 0.2757 | 437 | 5663 |
| 13 | 19.3000 | 4.59526 | 26 | 0.1952 | 224 | 2180 |
| 14 | 19.6942 | 4.50416 | 14 | 0.2776 | 127 | 1874 |
| 15 | 20.8600 | 4.25500 | 25 | 0.2542 | 216 | 3633 |
| 16 | 21.1479 | 4.19772 | 100 | 0.2253 | 876 | 9915 |
| 17 | 22.3600 | 3.97283 | 11 | 0.2734 | 94 | 1318 |
| 18 | 22.7003 | 3.91404 | 24 | 0.2776 | 206 | 3116 |
| 19 | 24.6375 | 3.61050 | 7 | 0.3250 | 63 | 1121 |
| 20 | 25.9103 | 3.43595 | 36 | 0.2628 | 312 | 4427 |
| 21 | 26.2200 | 3.39607 | 17 | 0.2284 | 148 | 1807 |

TABLE 2-continued

| peak no. | 2Theta (deg) | d (A) | I/I1 | FWHM (deg) | Intensity (Counts) | Integrated Int (Counts) |
|---|---|---|---|---|---|---|
| 22 | 27.5105 | 3.23962 | 6 | 0.2510 | 52 | 807 |
| 23 | 28.4600 | 3.13366 | 3 | 0.2400 | 30 | 413 |
| 24 | 29.2200 | 3.05386 | 3 | 0.2200 | 30 | 288 |
| 25 | 29.4183 | 3.03372 | 4 | 0.2367 | 38 | 463 |
| 26 | 31.6000 | 2.82907 | 3 | 0.3000 | 27 | 628 |
| 27 | 31.8200 | 2.81001 | 3 | 0.3466 | 30 | 466 |
| 28 | 34.1400 | 2.62418 | 4 | 0.5200 | 36 | 818 |
| 29 | 34.3200 | 2.61082 | 4 | 0.1534 | 37 | 255 |

These results revealed that the X-ray powder diffraction pattern, the infrared absorption spectrum, and the melting point of the crystal collected after storage were all different from those of the type A crystal. This crystal was named "type B crystal."

As described above, the type B crystal has a melting point higher than that of the type A crystal. This fact confirmed that the type B crystal has more excellent thermal stability. Before this analysis, a recrystallization method was performed using various solvents to search for crystals with more excellent stability than the type A crystal; however, different crystal types could not be found. Surprisingly, however, it was clarified that the type B crystal, which has higher stability (in particular, thermal stability), can be prepared by allowing the type A crystal to stand at a temperature higher than room temperature for a long period of time.

Type B Crystal Preparation 2

Analysis was conducted to further prepare the type B crystal using the obtained type B crystal as a seed crystal. More specifically, the type B crystal was prepared as follows, in accordance with the method disclosed in PTL 3 (WO2017/115780).

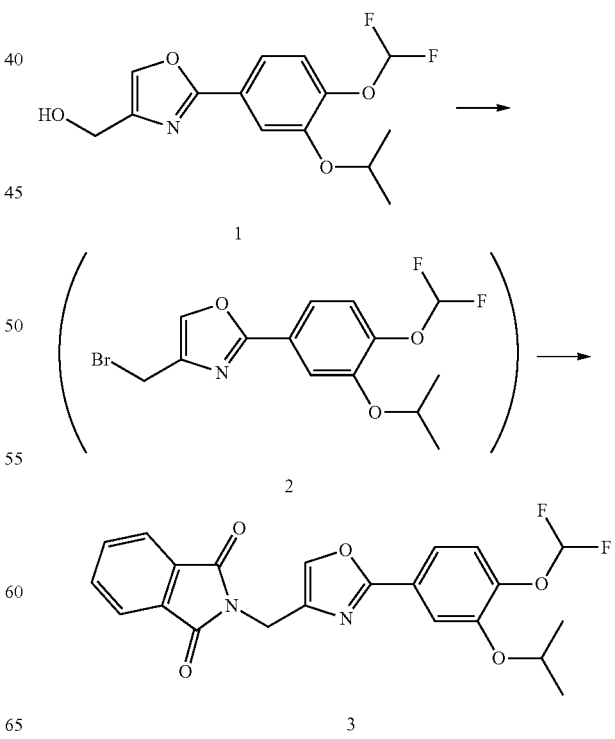

20.00 g (66.8 mmol) of compound (1) and 17.28 g (134 mmol) of diisopropylethylamine were added to 300 mL of ethyl acetate, and the mixture was cooled. 11.48 g (100 mmol) of methanesulfonyl chloride was poured in and stirred at 10 to 30° C. for 1 hour. 17.41 g (200 mmol) of lithium bromide was added thereto, and the mixture was stirred at 20 to 35° C. for 1 hour. 100 mL of water was added to the reaction solution, and the mixture was separated, followed by concentration of the organic layer under reduced pressure. 300 mL of ethyl acetate was added to the concentrated residue to dissolve the residue, and the solution was again concentrated under reduced pressure. 200 mL of N,N-dimethylformamide and 17.33 g (93.6 mmol) of potassium phthalimide were added to the concentrated residue, and reacted at 75 to 85° C. for 1 hour. 200 mL of water was added to the reaction solution to precipitate crystals. The precipitated crystals were collected by filtration and dried at 80° C., thereby obtaining 27.20 g (yield: 95.01%) of compound (3).

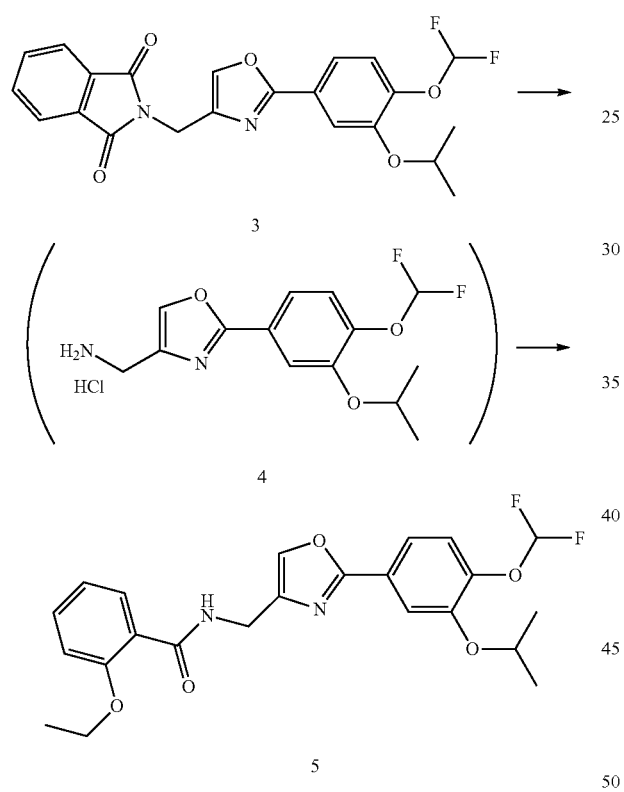

20.00 g (46.7 mmol) of compound (3), 40 mL of a 40% methylamine aqueous solution, 40 mL of methanol, and 100 mL of water were mixed and reacted for 30 minutes under reflux. 200 mL of cyclopentyl methyl ether (CPME) and 20 mL of a 25% sodium hydroxide aqueous solution were added to the reaction solution, and the temperature was adjusted to 65 to 75° C., followed by separation. A mixture of 100 mL of water and 20.00 g of sodium chloride was added to the organic layer, and the temperature was adjusted to 65 to 75° C. again, followed by separation. 5 mL of concentrated hydrochloric acid was added to the organic layer to precipitate crystals. The precipitated crystals were collected by filtration, thereby obtaining 27.58 g of compound (4) as a wet crystal.

The wet crystal (46.7 mmol) of compound (4) was mixed with 120 mL of ethyl acetate and 7.1 mL (51.4 mmol) of triethylamine, and stirred at 20 to 30° C. for 1 hour. 10.09 g (60.7 mmol) of 2-ethoxybenzoic acid and 11.63 g (60.7 mmol) of 1-ethyl-3-(3-dimethylaminopropyl)carbodiimide hydrochloride (WSC) were added to the reaction solution, and reacted at 20 to 30° C. for 1 hour. 60 mL of water and 6 mL of concentrated hydrochloric acid were added to the reaction solution, and the temperature was adjusted to 40 to 50° C., followed by separation. 60 mL of water and 6 mL of a 25% sodium hydroxide aqueous solution were added to the organic layer, and the temperature was adjusted to 40 to 50° C. again. The mixture was separated, and the organic layer was concentrated under reduced pressure. 50 mL of ethanol, 20 mL of water, 6 mL of a 25% sodium hydroxide aqueous solution, and 0.6 g of activated carbon were added to the concentrated residue, and the mixture was refluxed for 30 minutes. The activated carbon was removed by filtration, and the filtrate was washed with 12 mL of ethanol. The filtrate was cooled, and 10 mg of the type B crystal (a seed crystal) was added thereto to precipitate crystals. The precipitated crystals were collected by filtration and dried at 60° C., thereby obtaining 18.38 g (88.18%) of compound (5).

The X-ray powder diffraction pattern, the infrared absorption spectrum, and the melting point of the obtained crystal were measured as above. The results were all the same as the results above of the type B crystal. This confirmed that the type B crystal can be directly synthesized by using the type B crystal as a seed crystal, without the necessity of preparing the type B crystal by using the type A crystal.

The invention claimed is:
1. A method for producing a pharmaceutical composition containing a compound represented by formula (5),

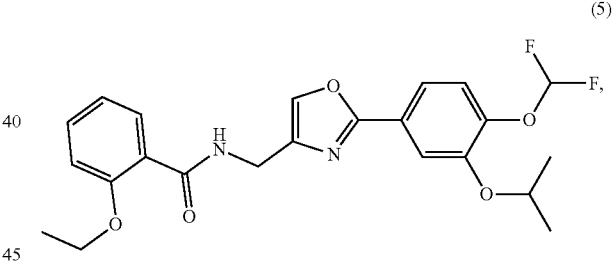

(5)

the method comprising dissolving a crystal of the compound,
wherein the crystal has peaks at diffraction angles 2θ(°) of 9.6±0.2, 12.6±0.2, 19.1±0.2, 21.2±0.2, and 22.8±0.2 in an X-ray powder diffraction pattern measured using CuKα characteristic X-rays.

2. The production method according to claim 1, wherein the crystal further has a peak at diffraction angle 2θ(°) of 26.0±0.2 in the X-ray powder diffraction pattern measured using CuKα characteristic X-rays.

3. The production method according to claim 2, wherein the crystal further has one or more peaks at one or more diffraction angles 2θ(°) selected from the group consisting of 10.4±0.2, 11.9±0.2, 15.0±0.2, 15.9±0.2, 19.7±0.2, 24.7±0.2, and 27.6±0.2 in the X-ray powder diffraction pattern measured using CuKα characteristic X-rays.

4. The production method according to claim 1, wherein the crystal has infrared absorption bands at wavenumbers (cm$^{-1}$) of 3380±5, 2980±5, 1651±2, 1501±2, 1258±2, 1121±2, and 754±2 in an infrared absorption spectrum measured by a potassium bromide disk method.

5. The production method according to claim 1, wherein the crystal has a melting point of 75 to 90° C.

6. The production method according to claim 1, comprising dissolving the crystal in a solvent by heating at a temperature equal to or higher than the melting point of the crystal.

7. The production method according to claim 6, comprising dissolving the crystal in a solvent by heating at a temperature of 85° C. or higher and 91° C. or lower.

8. The production method according to claim 1, comprising
   dissolving the crystal in a solvent, and
   mixing the solvent containing dissolved crystal with an ointment base.

9. The production method according to claim 8, wherein the solvent containing dissolved crystal in the pharmaceutical composition is dissolved or dispersed in the form of droplets in the ointment base.

10. The production method according to claim 8, wherein the solvent is a polar compound that is a liquid at room temperature.

11. The production method according to claim 8, wherein the ointment base comprises a hydrocarbon.

12. The production method according to claim 8, wherein the ointment base comprises at least beeswax.

13. The production method according to claim 9, wherein the droplets have a mean particle size of 100 μm or less.

14. The production method according to claim 1, which is a method for producing an ointment.

* * * * *